United States Patent

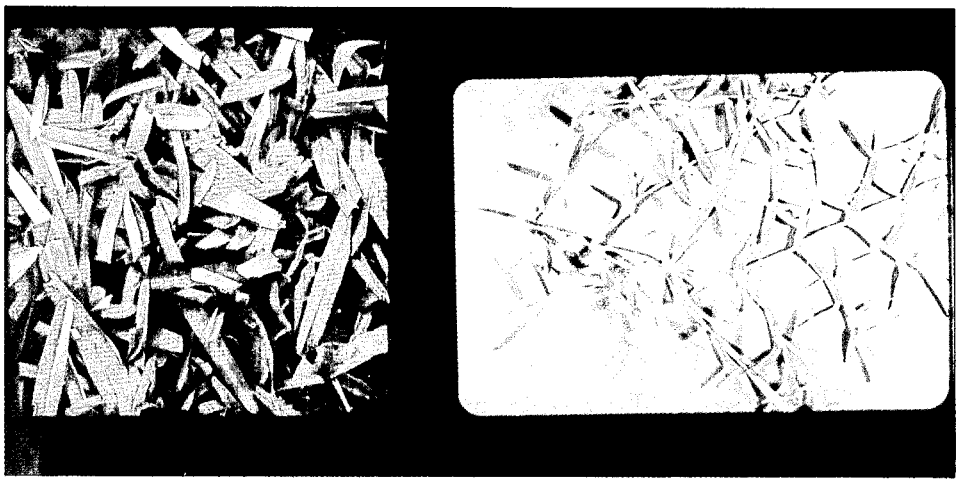
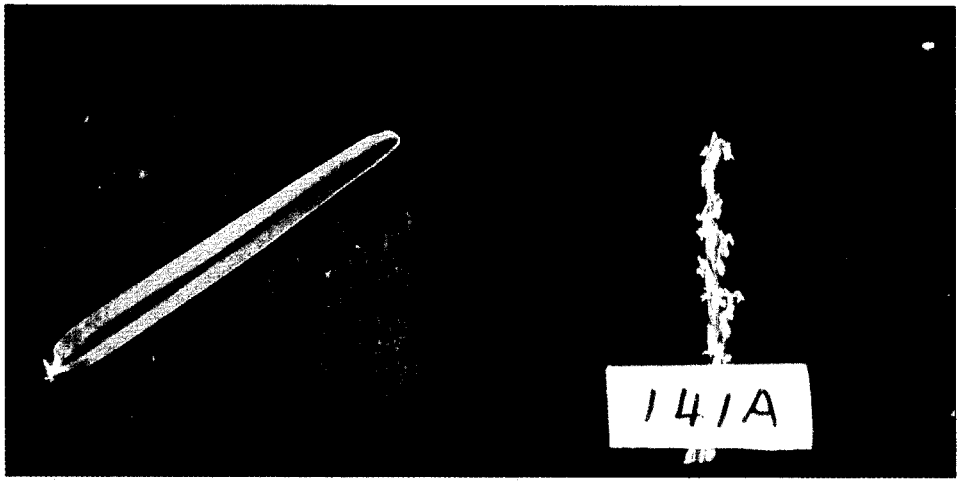
141A

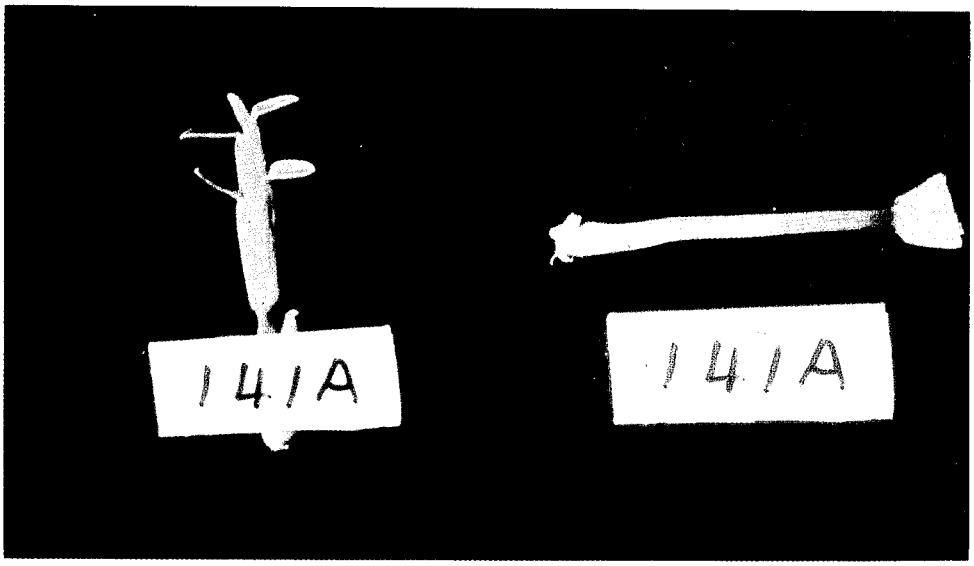
141A
141A
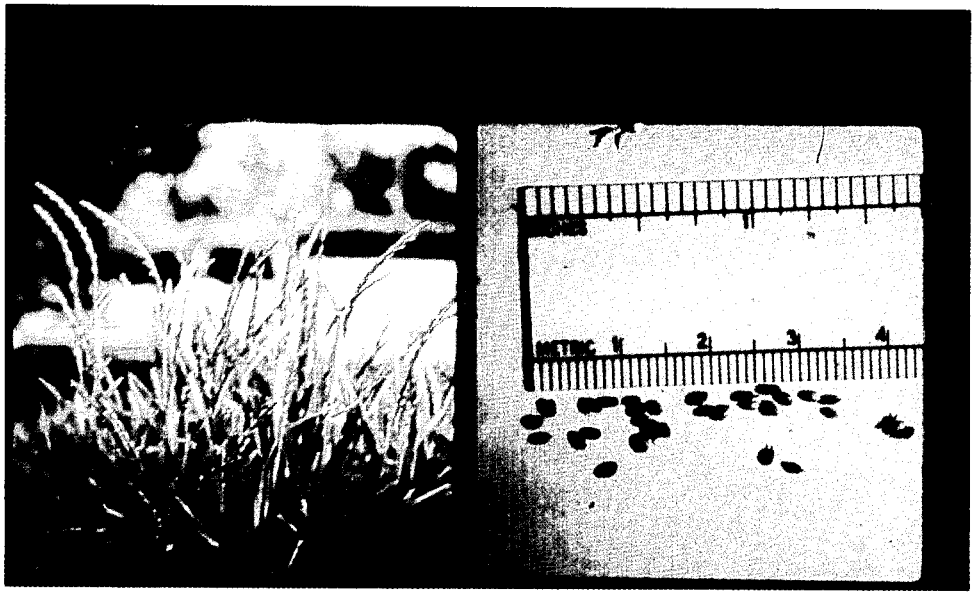
METRIC 1 2 3 4

Plant Pat. 3,834

Patented Mar. 2, 1976

3,834

ST. AUGUSTINE GRASS

Curran L. Garrett, P.O. Box 337, Ingleside, Tex. 78362

Filed Nov. 18, 1974, Ser. No. 524,966

Int. Cl. A01h 5/12

U.S. Cl. Plt.—88 1 Claim

The present invention relates to a new and distinct variety of St. Augustine grass which was discovered by me as a newly found seedling of unknown parentage which originated in the cultivated lawn of a homeowner located in Corpus Christi, Tex.

At the time of my discovery, I had been requested by the homeowner aforesaid to check and administer to the lawn of the aforementioned home property in Corpus Christi which was badly in need of attention. During my inspection and study of this lawn, I found that it was heavily infected with St. Augustine decline virus (SADV). However, at one location in the front lawn, my attention was attracted to a small patch of green grass, while all the rest of the lawn was very chlorotic. Upon close examination of the green patch, I found that the stolons of the individual plants were much smaller or finer than those of common St. Augustine grass, while the internodes were much shorter, and the stolons had a reddish pigmentation instead of the normal green color that is typical of common St. Augustine grass.

Accordingly, and with the permission of the homeowner, I removed several small runners from the green plot and transplanted them to pots which I generally identified as #141–A, B, C, etc., for future record purposes. These transplants rooted easily and grew vigorously. In due course, I asexually reproduced the new seedlings, in Corups Christi and elsewhere, as performed by me by the use of cuttings derived by cutting runners into short sections having at least 3 or 4 nodes and then planting the cuttings in pots with at least 2 of the nodes buried in the soil and with 1 or 2 nodes above the surface of the soil. These cuttings also put out new roots and grew very rapidly. These progeny and others have been extensively observed and tested, both in the fields and in the laboratory, including subjections to mechanical inoculations utilizing standard inoculation procedures. In the laboratory tests, my new seedling did not show any visible symptoms of SADV or any indication of susceptibility to such virus, but did show symptoms after being planted for two years or more in lawns that were highly infected with SADV. Despite this, the new seedling quickly recovered and resumed its normal thriving growth. Thus, although my new seedling is not immune to SADV, it has good tolerance to such viruses and is more resistant to many turf diseases than common St. Augustine grass, as determined by comparison with other varieties grown under the same conditions in Texas.

As the result of my extensive observations and tests which are only partially described in the foregoing for the sake of brevity, I am convinced that my new seedling is a new variety of St. Augustine grass which is distinguished from all other varieties of which I am aware, as evidenced by the following unique combination of principal characteristics which are outstanding therein:

(1) A low-growing and relatively flat or dwarf habit of growth except when allowed to seed, with the consequent production of excellent turf that is particularly attractive and suitable for lawn plantings;

(2) An ability to propagate very easily and rapidly from stolons, said stolons being smaller in diameter and reddish in color with white stigmas like all common St. Augustine grasses, and having shorter internodes than other varieties of St. Augustine grass;

(3) Good hardiness to temperatures as low as 15° F.;

(4) Heavy production of highly viable, fertile but heterozygous seed which germinate rapidly, said seed being borne in seed heads of a relatively uniform height of about 10 to 12 inches;

(5) Good tolerance to St. Augustine decline virus (SADV), with the ability to quickly recover from such virus when or if exposed to heavy infections thereof; and (6) Better resistance to many other turf diseases than common St. Augustine grass.

The accompanying drawings show a typical turf plot of plants of my new St. Augustine grass variety, as well as typical specimens of the runners, stolons, internodes, leaf blades, flowers, seed heads and seeds, all as depicted in color as nearly true as it is reasonably possible to make the same in a color illustration of this character. The true color of the foliage is described in the following description and is best depicted by the views of the specimen leaf blade and the runners, while the view of the seed specimens primarily illustrates the small size of the seed, rather than their details, and which, like the white stigmas (not shown) are not significantly distinctive. The view of the turf plot shows the low-growing and relatively flat habit of growth, while the view of the seed heads shows their relatively uniform height.

The following is a detailed description of my new St. Augustine grass variety, with color terminology in accordance with 1SCC-NBS Centroid Color Charts, except where general color terms of ordinary dictionary significance are obvious:

Growth habit: Low-growing stoloniferous; dwarf; fast-growing.

Culms: Branching; compressed.

*Flowering shoots.*—Up to 28.45 cm. long.

Stolons: Small; oval shaped.

*Color.*—Dark Gray Red, Color No. 20.

*Internodes.*—Oval shaped; primary stolon internodes 2.6 mm. x 1.9 mm. in cross section and average about 3.8 cm. in length; branch internodes 1.9 mm. x 1.5 mm. in cross section and average about 2.9 cm. in length.

Leaf blade: Leaves folded in the bud.

*Length.*—Total maximum length when uncut about 11.9 cm.; leaf length at the 5th or 6th internode where branches begin to join about 4.1 cm.

*Width.*—About 5.44 mm.

*Color.*— Medium Olive Green, Color No. 125.

*Venation.*—Obscure except the midrib which is prominent on the under side.

*Collar.*—Continuous; wide at the margins and narrow at the midrib. Color—White.

Ligule: A continuous fringe of hairs measuring about 0.2 mm. to 0.3 mm. long.

Auricles: Absent but represented by an intermittent fringe of white hair measuring about 0.65 mm. long and extended down the sheath for a distance of about 1.2 mm.

Inflorescence: A long fleshy raceme with about 28 embedded spikelets which are mostly fertile.

*Flowering shoots*—About 28.45 cm. long.

*Raceme.*—Average length about 8.97 cm.

*Spikelets.*—About 4.6 mm. long.

*First glume.*—About 1.92 mm. long.

*Second glume.*—About 3.82 mm. long.

*Palea.*—About 3.17 mm. long.

*Lemma.*—About 3.64 mm. long.

*Stigma.*—Color—White.

Seeds: Average about 449,000 seeds per pound; average 28 to 30 seeds per head and seeds are about 80% viable, with germination of 78% to 82%.

*Size.*—Length—About 1.95 mm. Width—About 1.2 mm. Thickness—About 0.7 mm.

GENERAL OBSERVATIONS

In addition to the ability of my new St. Augustine grass to propagate very easily and rapidly from stolons, it is also outstanding for its ability to abundantly produce highly viable, fertile but heterozygous seed which germinate rapidly. When these seed are planted at the rate of 10 oz. per 1000 sq. ft. of lawn area (2 seed per sq. in.), they will germinate in 6 to 8 days and produce 3 to 4 inch mowable turf in 21 days, and an established lawn in one month, instead of in 4 to 6 months as normally required with sprigging or sodding, and at about one-half the cost, including labor. Although seedlings produced from seeds of my new variety do not come absolutely true, they are sufficiently similar and suitable for sale of the seed as common St. Augustine grass seed which is not available to home owners up to the present time and thus becomes available for the first time as one of the important results of my new variety. Other outstanding features and distinctions of my new variety will be apparent from the foregoing description and the following comparative table.

I claim:

1. A new and distinct variety of St. Augustine grass, substantially as herein shown and described, characterized particularly as to novelty by the unique combination of a low-growing and relatively flat or dwarf habit of growth except when allowed to seed, with the consequent production of excellent turf that is particularly attractive and suitable for lawn plantings; an ability to propagate very easily and rapidly from stolons, said stolons being smaller in diameter and reddish in color with white stigmas and having shorter internodes than other varieties of St. Augustine grass; good hardiness to temperatures as low as 15° F.; heavy production of highly viable, fertile but heterozygous seed which germinate rapidly, said seed being borne in seed heads of a relatively uniform height of about 10 to 12 inches; good tolerance to St. Augustine decline virus (SADV), with the ability to quickly recover from such virus when or if exposed to heavy infections thereof; and better resistance to many other turf diseases than common St. Augustine grass.

COMPARATIVE TABLE

| Variety | Growth habit | Leaf color | Leaf length | Leaf width |
|---|---|---|---|---|
| 1. No. 141 | Low-growing | Medium olive green | 4.1 cm | 5.44 mm. |
| 2. No. 4,875 (Pl. pat. 3,491) | Upright | do | 13.86 cm | 7.14 mm. |
| 3. Floratam (npatented) | do | Comparable to bitter blue | 10.0 cm | 0.9 cm. |
| 4. No. 1,081 (Pl. pat. 2,863) | Low-growing | Moderate olive green | Less than 6.0 cm | 7.0 to 7.5 mm. |

| Variety | Internode color | Internode length | Internode diameter | Flower shoot height |
|---|---|---|---|---|
| 1. No. 141 | Dark gray red | Main 3.8 cm. Branch 2.9 cm | Main 2.6 x 1.9 mm. Branch 1.9 x 1.5 mm | 28.45 cm. |
| 2. No. 4,875 | do | 47.62 mm | 3.18 x 2.38 mm | 33 cm. |
| 3. Floratam | Dark red | 7.62 cm | | 30 to 45 cm. |
| 4. No. 1,081 | | | | 5 to 15 cm. |

| Variety | Raceme | Spikelets | First glume | Second glume | Palea |
|---|---|---|---|---|---|
| 1. No. 141 | 8.97 cm | 4.6 mm | 1.92 mm | 3.82 mm | 3.17 mm. |
| 2. No. 4,875 | 7.15 cm | 4.65 mm | 1.0 mm | 4.1 mm | 3.90 mm. |
| 3. Floratam | | | | | |
| 4. No. 1,081 | 5 to 10 cm | 3.2 to 3.3 mm | 1.07 to 1.11 mm | 3.0 to 3.06 mm | 2.96 to 3.02 mm. |

| Variety | Lemma | Stigma color | Average spikelets per raceme | Seed size |
|---|---|---|---|---|
| 1. No. 141 | 3.64 mm | White | 28 | 1.99 mm. long. 1.2 mm. wide. 0.7 mm. thick. |
| 2. No. 4,875 | 4.0 mm | Purple with white filament | | |
| 3. Floratam | | Purple | | |
| 4. No. 1,081 | 3.09 to 3.39 mm | do | | |

No references cited.

ROBERT E. BAGWILL, Primary Examiner